US00PP09277P

United States Patent [19]

Dehan

[11] Patent Number: Plant 9,277

[45] Date of Patent: Sep. 5, 1995

[54] IMPATIENS PLANT NAMED 'TWINY GINI'

[75] Inventor: Klara Dehan, Holon, Israel

[73] Assignee: Danziger "Dan" Flower Farm, Hashiva, Israel

[21] Appl. No.: 298,980

[22] Filed: Sep. 2, 1994

[51] Int. Cl.[6] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Foley & Lardner

[57] ABSTRACT

A new and distinct cultivar of Impatiens plant named Twiny Gini, characterized by its small dark green leaves and small bicolor flowers, with the flowers standing well above the leaves, red flower color with non-uniform white spotting; excellent self-branching and compact growth habit, and its very early flowering.

1 Drawing Sheet

The present invention relates to a new and distinctive cultivar of impatiens plant, botanically known as Impatiens, commercially known as New Guinea Impatiens, and known by the cultivar name Twiny Gini.

The new cultivar was developed by the inventor Klara Dehan in Mishmar Hashiva, Israel in a controlled breeding program. The female or seed parent was a cultivar identified by the breeding number 144 WM, and the male or pollen parent was a cultivar identified by the breeding number 113 OR. Both parents are proprietary cultivars used in the breeding program. The new cultivar was selected by the inventor from the progeny of the stated cross.

Asexual reproduction of the new cultivar by leaf cuttings performed by the inventor in Mishmar Hashiva, Israel has established that the unique features of this new impatiens are stabilized and are reproduced true to type in successive propagations.

The following charactertistics in combination distinguish the new Impatiens Twiny Gini from both its parent varieties and other cultivated impatiens of this type known and used in the floriculture industry:

1. The primary distinguishing feature is the relatively small flowers, with the flowers standing well above the leaves.
2. The flowers are bicolored, including a generally rose red main color with white spots on the petals.
3. The relatively small leaves are shiny dark green in color.
4. Excellent self-branching.
5. Floriferous habit and early flowering.
6. The cultivar can be propogated by leaf cuttings year around.

The accompanying color photographic drawing illustrates the overall appearance of the cultivar, with the colors being as true as it is reasonably possible to obtain in a colored reproduction of this type.

The following is a detailed description of the new impatiens cultivar based on plants produced under commercial practice in Mishmar Hashiva, Israel. The plants described were grown in a net-covered greenhouse during the summer season with temperatures ranging from 35° C. maximum to 18° C. minimum. Color references are made to The Royal Horticultural Society Colour chart except where general terms of ordinary dictionary significance are used.

Parentage: The female parent 144 WM and the male parent 113 OR are seedlings from breeding program.

Propagation:

*Type cutting.*—Leaf cuttings.

*Time to initiate roots.*—7–8 days at 25° C. in summer; 9–10 days at 20° C. in winter.

*Rooting habit.*—Roots well.

Plant description:

*Form.*—Excellent self-branching produces a full, rounded symmetrical plant particularly suitable for small pots 7–10 cm in diameter.

*Habit of growth.*—Compact growth habit.

*Foliage.*—Size: Small; mature leaves 8.0 cm long and 3.0 cm wide. Shape: Lanceolate to ovate. Margin: Serrated. Color: Young and mature foliage, top side 147A; under side 147B. Venation: Main vein is reddish and side veins are light green.

Flowering description:

*Flowering habits.*—The initiation of flower buds takes about 5 weeks from potting leaf cutting. Flowering is early, with flowers being completely open approximately 7–8 weeks after potting.

*Natural flowering season.*—The new cultivar flowers under ambient conditions in Israel all year, but in the winter season with less light, there are fewer flowers.

*Flower buds.*—Buds before opening are approximately 1.0 cm in length and 1.0 cm in width. Length of spur is 3.0 cm, and length of pedicel is 3.0 cm.

*Flowers borne.*—Flowers fully open from bud stage in about 2 weeks, and flowering thereafter continues all season.

*Quantity of flowers.*—Very floriferous, with 30–40 flowers open at the same time, as shown in the photograph; flowering is continuous.

*Petals.*—Shape: Two (2) pairs of heart-shaped petals and a single larger petal; petals overlap. Color: Top side when opening 50A with areas of white spotting 55D; location and amount of white variegation can vary from petal to petal as clearly shown in photograph; very little fading of main color; under side 43C. Number of petals: Five (5). Size of flowers: Very small, about 3.0 cm in diameter.

*Reproductive organs.*—Stamens: One (1 ) in number. Anthers: Round, light red color. Pollen color: White. Pistils: Stigma: Round in shape, nearly white in color. Ovaries: Four (4) in number, 1 mm in size, light green in color.

Disease resistance: No significant disease problem noted to date.

I claim:

1. A new and distinct cultivar of Impatiens plant named Twiny Gini, as illustrated and described.

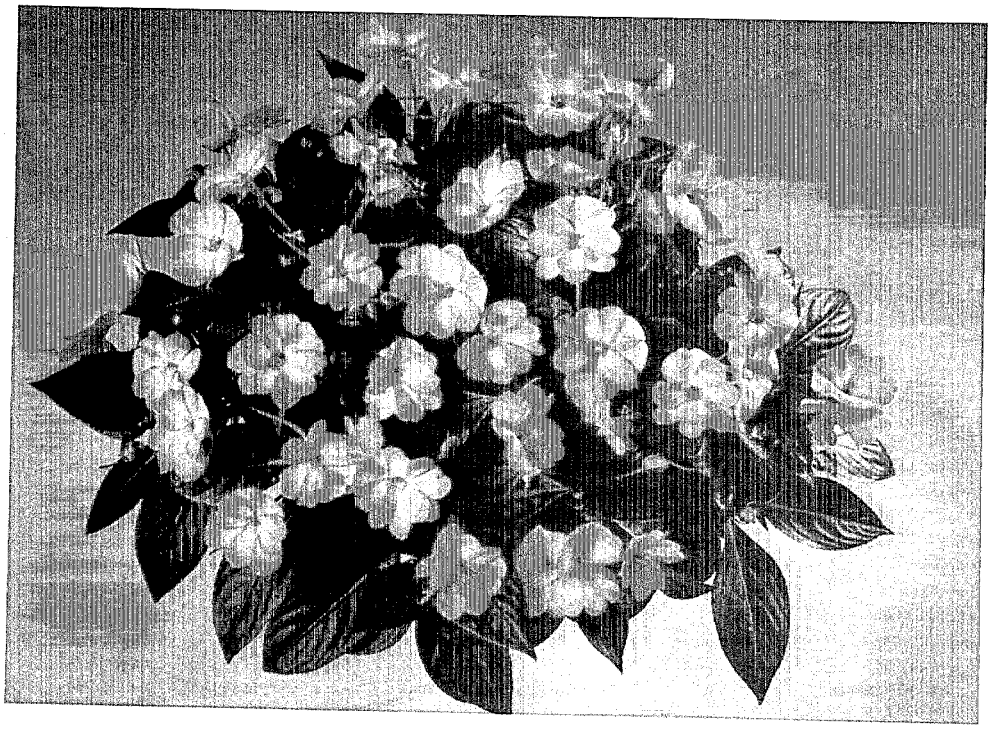

* * * * *